(12) United States Patent
Carlsson et al.

(10) Patent No.: US 6,591,698 B1
(45) Date of Patent: Jul. 15, 2003

(54) SURGICAL INSTRUMENT WITH MEANS TO DISPLAY TORQUE AND TORSIONAL ANGLE

(75) Inventors: Lennart Carlsson, Mölndal (SE); Anders Petersson, Göteborg (SE)

(73) Assignee: Nobel Biocare AB, Gothenburg (SE)

( * ) Notice: Subject to any disclaimer, the term of this patent is extended or adjusted under 35 U.S.C. 154(b) by 0 days.

(21) Appl. No.: 09/319,220

(22) PCT Filed: Dec. 15, 1997

(86) PCT No.: PCT/SE97/02096
§ 371 (c)(1), (2), (4) Date: Jul. 21, 1999

(87) PCT Pub. No.: WO98/27886
PCT Pub. Date: Jul. 2, 1998

(30) Foreign Application Priority Data

Dec. 20, 1996 (SE) ................................................ 9604717

(51) Int. Cl.⁷ ................................................ G01L 3/22
(52) U.S. Cl. ................................................ 73/862.18
(58) Field of Search ........................ 73/862.23, 862.18, 73/862.21, 862.27; 364/510; 433/27; 606/82; 609/99

(56) References Cited

U.S. PATENT DOCUMENTS

| | | | | |
|---|---|---|---|---|
| 3,831,072 A | * | 8/1974 | Tanikoshi | 318/138 |
| 3,898,875 A | * | 8/1975 | Knoop et al. | 73/116 |
| 4,402,052 A | * | 8/1983 | Stone et al. | 364/506 |
| 4,446,745 A | * | 5/1984 | Stone et al. | 73/862.25 |
| 5,303,601 A | * | 4/1994 | Schonberger et al. | 73/862.23 |
| 5,402,688 A | * | 4/1995 | Okada et al. | 73/862.23 |
| 5,538,423 A | * | 7/1996 | Coss et al. | 408/8 |
| 5,614,948 A | * | 3/1997 | Hannah | 348/222 |
| 5,689,434 A | * | 11/1997 | Tambini et al. | 364/510 |
| 5,869,752 A | * | 2/1999 | Klauber et al. | 73/116 |
| 5,898,112 A | * | 4/1999 | Dawood | 73/862.23 |
| 5,904,689 A | * | 5/1999 | Jonjic | 606/99 |
| 6,261,293 B1 | * | 7/2001 | Nicholson et al. | 606/79 |
| 6,285,902 B1 | * | 9/2001 | Kienzle et al. | 378/20 |

FOREIGN PATENT DOCUMENTS

| | | |
|---|---|---|
| GB | 2 098 740 A | 11/1982 |
| GB | 2098740 | 11/1982 |
| GB | 2286127 | 8/1995 |
| GB | 2 286 127 A | 8/1995 |
| WO | WO 95/20146 | 7/1995 |

\* cited by examiner

*Primary Examiner*—Max Noori
*Assistant Examiner*—Jewel V. Thompson
(74) *Attorney, Agent, or Firm*—Connolly Bove Lodge & Hutz LLP; Stanley B. Green

(57) ABSTRACT

A surgical instrument (12) includes a tool for screwing in a surgical implant or for cutting a thread in human bone tissue with thread tap. Also included is a unit (2) for supplying power and controlling the speed of an electric motor included in the tool, for example a d.c. motor (1). Detection members (7, 8) transmit signals (i1), dependent on the torque of the tool, to display members which comprise a computer unit (9) with screen (10). Displayed on the screen is a curve which shows the torque in relation to the torsional angle position. A curve or curves displayed in this way form(s) the basis for assessing the quality of the implant or of the bone tissue.

5 Claims, 2 Drawing Sheets

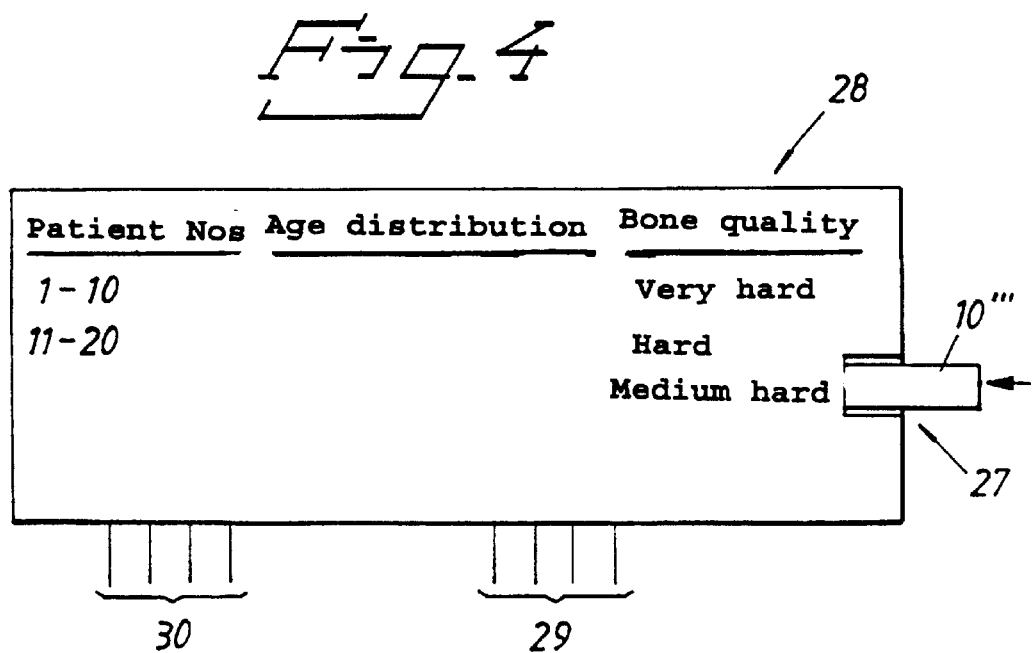
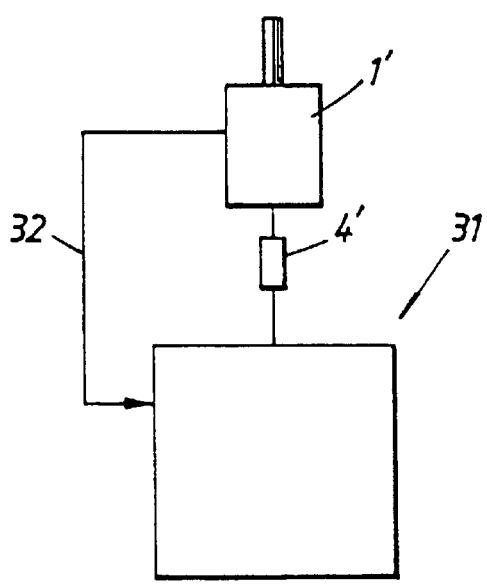
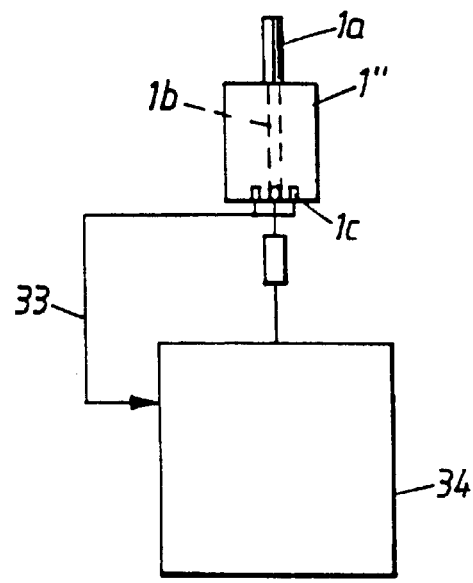

SURGICAL INSTRUMENT WITH MEANS TO DISPLAY TORQUE AND TORSIONAL ANGLE

TECHNICAL FIELD

The present invention relates to a surgical instrument which comprises, inter alia, a tool for screwing in a surgical implant or for cutting a thread in human bone tissue with thread tap. Also included is a unit for supplying power and controlling the speed of an electric motor included in the tool, and detection and display members, the detection members transmitting signals, dependent on the torque and torsional angle of the tool, to the display members. The latter comprise a computer unit, for example a microprocessor, with associated display and memory members, which respectively display and store a torque curve effected by the tool on the basis of the screwing-in or thread-cutting. This curve shows the torque as a function of the torsional angle. The display member can in this case be of the type which comprises a computer screen, VDU, etc. The invention also relates to an arrangement in which the above surgical instrument is included.

PRIOR ART

It is already known, for example from PCT publication WO 95/20146, to use, in screwing tools, a unit for supplying power to an electric motor. An amplifier is connected to the current supply circuit of the electric motor, and this amplifier is followed by an analog/digital converter. The latter is in turn connected to a computer unit with VDU. It is also already known per se to investigate various bone qualities of the human body and to draw up statistics on these bone qualities. In this case it is possible to detect the capacity of a particular tool to penetrate the respective bone/bone tissue, and to relate the penetration capacity to the bone quality. It is also known to use torque-controlled tools for screwing and thread-cutting in conjunction with dental work using implants, dental bridge structures, etc. Different evaluations of bone quality for different persons of different ages are known per se.

DESCRIPTION OF THE INVENTION

Technical Problem

There is a need for effective means for aiding surgeons, dentists and equivalent personnel performing advanced dental work. For example, when cutting a thread and fitting a screw, the surgeon or equivalent person must have complete control of the work being carried out. The implant and dental structure in question must be applied optimally. This optimal application is to a large extent dependent on the quality of the bone tissue in each individual case, which quality is not always entirely apparent from external inspection. Hitherto, a good result has been associated with professional skill and experience. The present invention solves the problem by indicating with great precision, for example, the bone quality, strength of the screw material, etc.

When drawing up statistics and other information, it is important to be able, in a simple manner, to document the respective work performed in respect of bone quality, patient type, age, type of structure, implant application, etc. The invention solves this problem too.

It is also important that the operating function of the tool in question can be given a simple and well proven function and component design. The invention solves these problems too. The invention uses the fact that the torsional angle is known.

Solution

The feature which can principally be regarded as characterizing a surgical instrument according to the invention is that the detection member or the detection members transmit(s) signals, dependent on the torque and angle position(s) of the tool, to the display members which comprise a computer unit which, besides the display member, has memory members, and that the display member is arranged in this case to display a torque/torsional angle curve, which forms the basis for assessing the quality of the implant/bone tissue.

In one embodiment, the unit for supplying power and controlling the speed is arranged to provide the electric motor with an essentially constant speed of rotation or a known variable speed of rotation.

With the torque/torsional angle curve it is also possible to check if the screw material is of good quality and that the elasticity limits in question are not being exceeded. The said storage member/members is/are arranged to store one or more torque curves which can be related to different screwing-in and/or thread-cutting cases.

In one embodiment, the detection member comprises an amplifier and, connected-in downstream of this, an analog/digital converter which converts the signals of the detection member into corresponding data signals. The said data signals are shown, with the aid of low-pass filtering, as a histogram on the display member's screen, where each column corresponds to a number of mean values of the torque in order that rapid variations or ripples will not disturb production.

The arrangement according to the invention is characterized essentially in that detection members detect torque(s) effected by the tool and relate this to the torsional angle position or torsional angle positions, and in that a display member or display members is/are arranged to display a curve which shows the torque variation as a function of the torsional angle position, and in that the display member/members comprises/comprise or is/are connected to one or more storage members. Further characteristics are that the arrangement also comprises an evaluation system for bone quality, statistics on bone qualities, etc., and that the said storage member/members is/are arranged to store one or more torque/torsional angle curves. The stored curves are further arranged such that they can be transferred to the evaluation system.

In a preferred embodiment, a removable storage member is used as storage member. The storage member can here have the form of a card which can be loaded with data (cf. credit card, electronic wallet card, etc.). The respective curve formation for one or more patients is fed into the card in question. After the data information has been loaded, the card can be removed for use, i.e. insertion, in the evaluation system.

Advantages

With the above functions built into a surgical instrument, which additionally has facilities for cooling, speed control, direction of rotation control, torque control, etc., a very attractive technical support instrument for the surgeon or equivalent is obtained.

DESCRIPTION OF THE FIGURES

A presently proposed embodiment of a surgical instrument and arrangement according to the invention will be described below with reference to the attached drawings, in which:

FIG. 4 shows, in a horizontal; view, an evaluation system, FIG. 5 shows, in a basic circuit diagram, a speed control for the electric motor in question in the tool, and FIG. 5a shows, in a basic circuit diagram, speed control and information on the torsional angle of the rotor by means of magnet and Hall elements and a calculator coupled to the computer.

DETAILED EMBODIMENT

Figure 1:
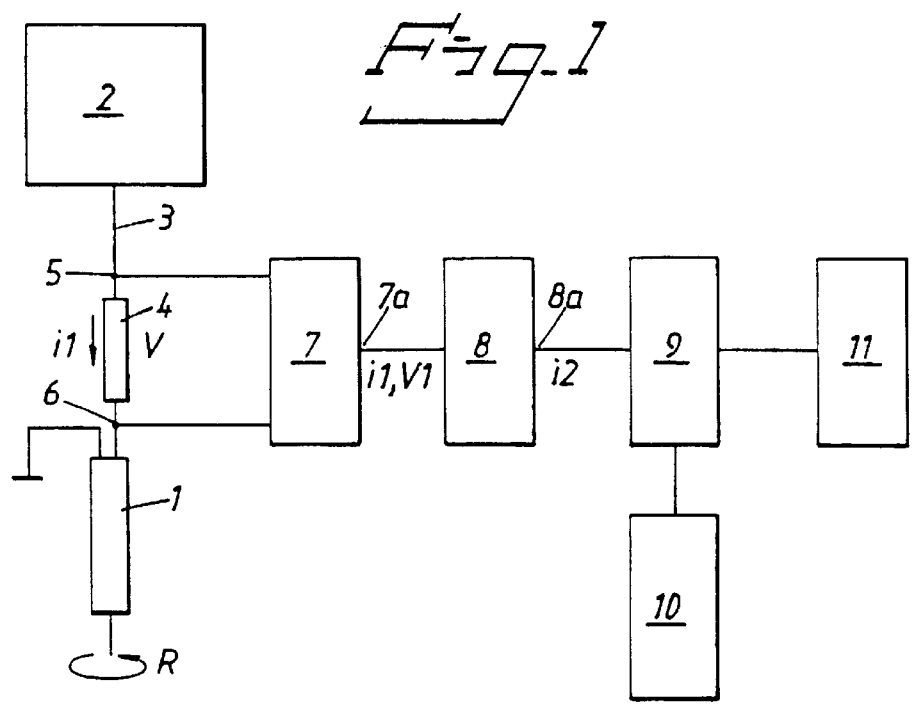
FIG. 1 shows, in a basic circuit diagram, the functions of the tool's electric motor, its power and speed control, detection members for the electric motor's torque/torsional angle curve, and display members and storage members for the curve or curves in question.

In FIG. 1, an electric motor is symbolized by 1. The motor is of a type known per se and can be of the brushless EC 032 type which is sold on the open market by Stork AB. A combined electrical power and speed control unit is shown by 2. The unit is arranged, inter alia, so that it can provide the motor 1 with a constant speed of rotation independently of the torque of the motor. Alternatively, or in addition to this, it can measure the torsional angle in a known manner with the aid of Hall elements and a magnet on the rotor. Arranged in the current supply circuit 3 of the motor there is an element 4, preferably in the form of a resistor. An amplifier 7 of known type is connected at contact points 5, 6 across the resistor. The output 7a of the amplifier is connected to an analog/digital converter 8 whose output 8a is connected to a computer unit 9, for example a microprocessor, which comprises a storage member 10 and a display screen 11, for example in the form of a VDU.

The motor 1 comprises in a known manner a gear and rotates in accordance with the above at a constant speed of rotation or with a rotor position 1 which is known at each instant. The supply current through the resistor is shown by i1. The amplifier detects the voltage V across the resistor and conveys a current i1/voltage V1 dependent on the changes to the analog/digital converter, which effects a pulse train i2 dependent on the detection. The computer unit 9 receives the said pulse train.

In this way, when threading-in an implant or screwing-in a screw in dental constructions, the voltage drop across the resistor is displayed in real time on the said display. As the motor current is proportional to the voltage drop and the current is in turn proportional to the transmitted torque, a direct display of the latter is obtained. The torque is shown on the display as a function of the time. Data (i2) is shown as an analog curve (torque as a function of torsional angle). The curve undergoes low-pass filtering so that the rapid variations or electrical ripple will not be seen. The said ripple, which consists of small irregularities superimposed on the curve, is caused by irregularities in the gearbox and motor commutations.

Figure 2:
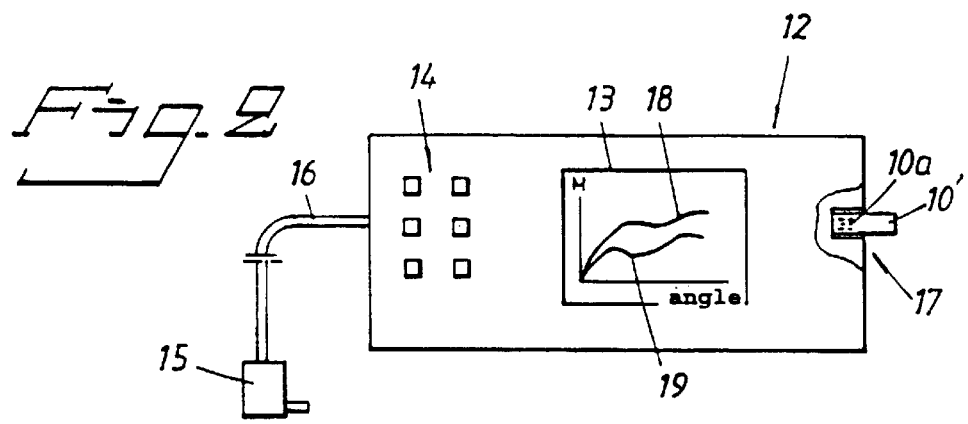
FIG. 2 shows, from the front, an example of a surgical instrument.

FIG. 2 shows a surgical instrument 12 in its entirety. The instrument display (i.e. the computer screen in accordance with the above) is shown by 13. The instrument has a keyboard/indication panel 14 for different functions, cf. above. The tool is indicated by 15, and a connection to the tool is indicated by 16. The storage member in accordance with the above has here been designated 10'. The storage member is designed as a credit card (cf. electronic wallet) which can be loaded with data. The card can be inserted into and removed from a card-reading unit 17 in a known manner. The card has an integrated circuit 10a which can be provided in a known manner with data, i.e. in this case torque data as a function of the tool position (angle).

In the figure, two torque curves 18, 19 are shown on the screen 13, these curves each representing thread-cutting or screwing-in of the implant in the jaw/bone tissue. The curves indicate the moment M as a function of the position of rotation/torsional angle. The higher the torque values, the higher the shearing force, which can be linked to bone quality.

Figure 3:
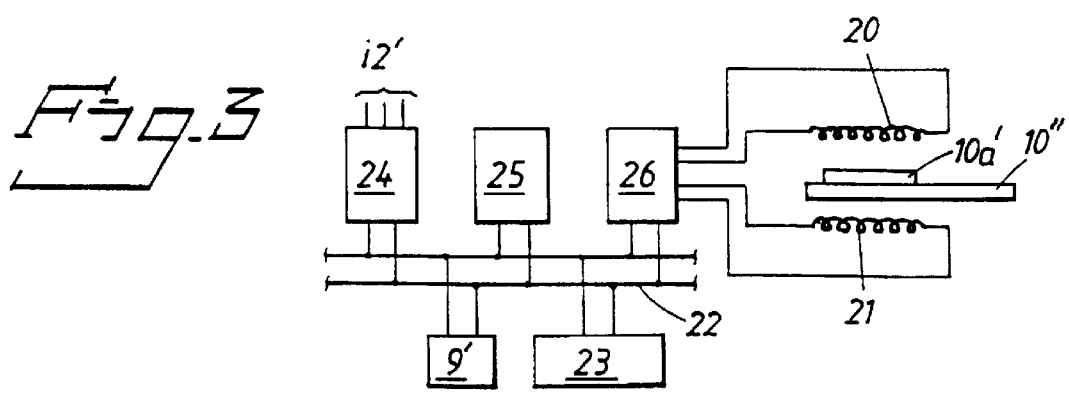
FIG. 3 shows, in a basic circuit diagram, the input functions for a card which can be loaded with data on torque/torsional angle curves.

The card 10 is shown from the side in FIG. 3, where the loading members/circuits have been symbolized by 20, 21. A bus connection is shown by 22, and a micro-processor (CPU) in accordance with the above, indicated by 9', is connected to this bus connection 22. A terminal 23 connected to the bus connection can also be included, on which terminal 23 it is possible to input data supplementing the torque curves, for example in the form of date, patient type, age, etc. The pulse train i2' is received via an adaptor circuit 24 connected to the bus connection. Also included are an associated fixed memory 25 and an adaptor member 26 for the loadable memory 10', 10a'. The components 25 and 26 are also connected to the bus connection.

According to FIG. 4, the card/memory 10''' can be introduced into a card reader 27 of known type on or in the evaluation system. Statistics, assessment of bone quality, etc. can be carried out in the latter and collected. The information on this can be obtained at the outputs 29, 30.

In FIG. 5, a combined supply and speed control unit (for example, in the form of Hall elements-magnet-calculator-computer, cf. 2 above) for the motor 1' is shown by 31. A position indication feedback is shown by 32, and the resistor in accordance with the above is shown by 4'. The speed of rotation is measured with Hall elements.

Speed control and information on the angle position of the rotor 1a are obtained, for example, by using a magnet 1b on the rotor of the motor, and three Hall elements 1c which detect the position of the magnet. The Hall elements are coupled via a feedback circuit 33 to a calculator circuit 34 which in turn is coupled to a computer. For example, the control circuit MMC-EC050 Stork AB) which is coupled to a calculator circuit. The motor is, for example, EC032 (Stork AB).

The invention is not limited to the embodiment shown above by way of example, but can be modified within the scope of the attached patent claims and the inventive concept.

What is claimed is:

1. Surgical instrument (12) comprising:
    a tool (15) for cutting a thread in bone tissue with a thread tap;
    a unit (2) for supplying power and controlling a speed of an electric motor (1) included in the tool;
    a computer unit (9) having a storage member (10) and a display member; and
    a detection means (7, 8), connected to the tool, for detecting torque and angle position(s) of the tool, wherein,
        the detection means transmit signals (i2), dependent on the detected torque and angle position(s) of the tool, to the computer unit, and
        the display member displays a torque/torsional angle curve, which forms a basis for assessing a quality of the bone tissue.

2. Surgical instrument according to claim 1, wherein:
    the unit for supplying power and controlling the speed is arranged to provide the electric motor with an essentially constant speed of rotation or a known variable speed of rotation.

3. Surgical instrument according to claim 1, wherein:

the storage member (10) is arranged to store a number of torque/torsional angle curves (13, 18) which can be related to different thread-cutting cases.

4. Surgical instrument according to claim 1, wherein:

the detection means comprises:
  an amplifier (7) that amplifies detected torque and angle position signals of the tool; and
  an A/D converter (8) connected downstream of the amplifier that converts signals (i1) of the detection means into corresponding data signals (i2); and the data signals (i2) are shown as a histogram on a screen (11) of the display member, where each column of the histogram corresponds to a number of mean values of the torque dependent on the torsional angle position, so that rapid variations or ripples will not be seen.

5. Surgical instrument according to claim 1, wherein:

the speed control and the determination of information on a position/rotational position of a rotor of the electric motor are carried out by a magnet, Hall elements, a converter, and the computer unit.

* * * * *